(12) United States Patent
Hafezi et al.

(10) Patent No.: US 10,653,875 B2
(45) Date of Patent: May 19, 2020

(54) INGESTIBLE DEVICE WITH PHARMACEUTICAL PRODUCT

(71) Applicant: Proteus Digital Health, Inc., Redwood City, CA (US)

(72) Inventors: Hooman Hafezi, Redwood City, CA (US); Raymond Schmidt, San Francisco, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 286 days.

(21) Appl. No.: 15/491,409

(22) Filed: Apr. 19, 2017

(65) Prior Publication Data

US 2017/0216569 A1 Aug. 3, 2017

Related U.S. Application Data

(62) Division of application No. 14/829,229, filed on Aug. 18, 2015, now abandoned, which is a division of application No. 13/521,993, filed as application No. PCT/US2011/061478 on Nov. 18, 2011, now Pat. No. 9,107,806.

(60) Provisional application No. 61/416,150, filed on Nov. 22, 2010.

(51) Int. Cl.
*A61M 31/00* (2006.01)
*A61K 9/00* (2006.01)
*A61K 9/48* (2006.01)
*A61J 3/07* (2006.01)
*A61B 5/145* (2006.01)
*A61B 5/00* (2006.01)

(52) U.S. Cl.
CPC ....... *A61M 31/002* (2013.01); *A61B 5/14503* (2013.01); *A61B 5/4833* (2013.01); *A61J 3/071* (2013.01); *A61K 9/0097* (2013.01); *A61K 9/4808* (2013.01); *A61M 2205/0238* (2013.01); *A61M 2205/33* (2013.01); *A61M 2205/50* (2013.01); *A61M 2205/82* (2013.01); *A61M 2207/00* (2013.01); *Y10T 29/49826* (2015.01)

(58) Field of Classification Search
CPC .... A61B 5/14503; A61J 3/071; A61K 9/4808; A61M 2205/0238; A61M 2205/33; A61M 31/002
See application file for complete search history.

(56) References Cited

U.S. PATENT DOCUMENTS

| | | | |
|---|---|---|---|
| 6,942,770 B2 | 9/2005 | Cai et al. | |
| 8,177,611 B2 | 5/2012 | Kang | |
| 8,784,308 B2 * | 7/2014 | Hafezi | A61J 3/06 600/300 |
| 9,968,284 B2 | 5/2018 | Vidalis et al. | |
| 2002/0099423 A1 | 7/2002 | Berg et al. | |

(Continued)

*Primary Examiner* — Deanna K Hall
(74) *Attorney, Agent, or Firm* — K&L Gates LLP

(57) ABSTRACT

A pharmaceutical product including a housing that defines a cavity, wherein the cavity stores a pharmaceutical material, and wherein the housing comprises a material configured to dissolve based on contact with a fluid, an ingestible device to encode information in a current signature, wherein the ingestible device is positioned within the housing, and a protective material that encompasses the ingestible device. The ingestible device may be attached to a flexible component, wherein the flexible component is configured to releasably secure the ingestible device within the housing.

20 Claims, 5 Drawing Sheets

(56) References Cited

U.S. PATENT DOCUMENTS

| | | |
|---|---|---|
| 2002/0128934 A1 | 9/2002 | Shaer |
| 2004/0117062 A1 | 6/2004 | Bonney et al. |
| 2006/0122494 A1 | 6/2006 | Bouchoucha |
| 2007/0029195 A1 | 2/2007 | Li et al. |
| 2009/0047357 A1 | 2/2009 | Tomohira et al. |
| 2009/0194747 A1 | 8/2009 | Zou et al. |
| 2009/0197068 A1 | 8/2009 | Yamaguchi et al. |
| 2012/0276451 A1 | 11/2012 | Lestriez et al. |
| 2013/0131283 A1 | 5/2013 | Wang et al. |
| 2013/0209877 A1 | 8/2013 | Kren et al. |
| 2013/0275296 A1 | 10/2013 | Tietzen et al. |
| 2015/0017486 A1 | 1/2015 | Lai |
| 2018/0184698 A1 | 7/2018 | Arne et al. |
| 2018/0214048 A1 | 8/2018 | Zdeblick et al. |
| 2018/0229996 A1 | 8/2018 | Thompson |
| 2019/0158151 A1 | 5/2019 | Shirvani et al. |

\* cited by examiner

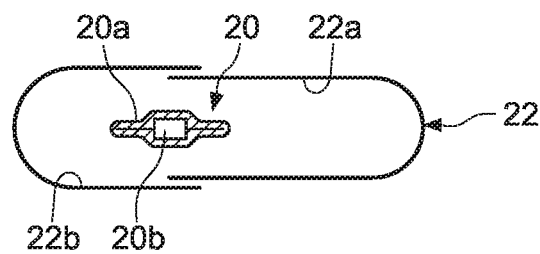
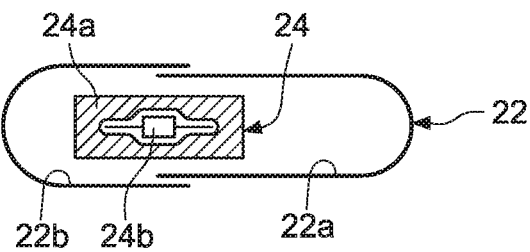
FIG. 1
FIG. 2A
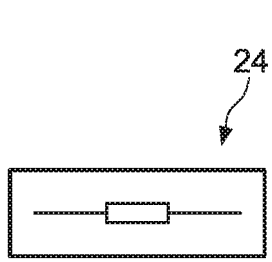
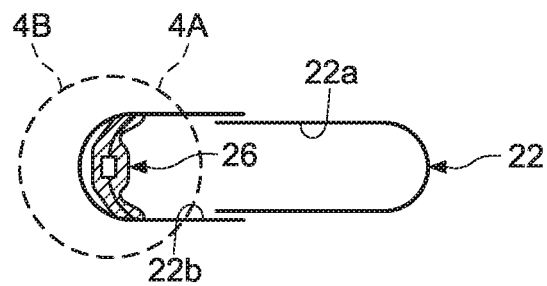
FIG. 2B
FIG. 3
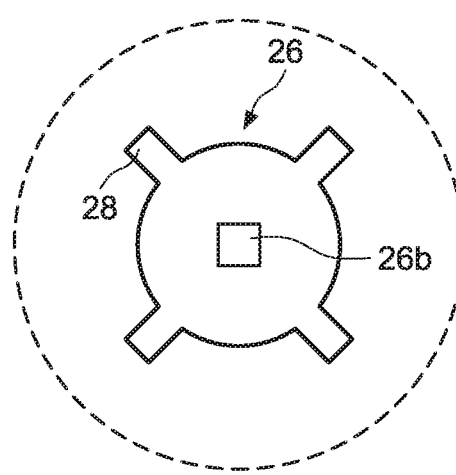
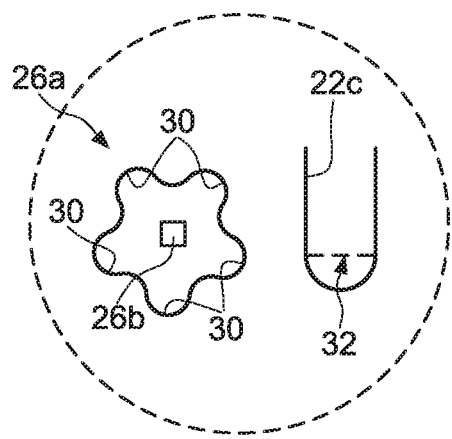
FIG. 4A
FIG. 4B

INGESTIBLE DEVICE WITH PHARMACEUTICAL PRODUCT

CROSS-REFERENCE TO RELATED APPLICATIONS

This application is a divisional application claiming priority under 35 U.S.C. § 121 to U.S. patent application Ser. No. 14/829,229, entitled INGESTIBLE DEVICE WITH PHARMACEUTICAL PRODUCT, filed Aug. 18, 2015, now U.S. Patent Application Publication No. 2015/0352343, which is a divisional application claiming priority under 35 U.S.C. § 121 to U.S. patent application Ser. No. 13/521,993, entitled INGESTIBLE DEVICE WITH PHARMACEUTICAL PRODUCT, filed Jul. 12, 2012, now U.S. Pat. No. 9,107,806, which is a U.S. National Stage Entry under 35 U.S.C. § 371 of International Patent Application No. PCT/US2011/061478, entitled INGESTIBLE DEVICE WITH PHARMACEUTICAL PRODUCT, filed Nov. 18, 2011, which claims the benefit under 35 U.S.C. § 119(e) of U.S. Provisional Patent Application Ser. No. 61/416,150, entitled INGESTIBLE DEVICE WITH PHARMACEUTICAL PRODUCT, filed Nov. 22, 2010, the entire disclosures of which are hereby incorporated by reference herein.

RELATED APPLICATIONS

This application is related to and incorporates the following applications by reference: U.S. patent application Ser. No. 14/570,673, now published as U.S. Patent Application Publication No. 2015/0182463 and entitled CONTROLLED ACTIVATION INGESTIBLE IDENTIFIER, U.S. Pat. No. 8,945,005 issued on Feb. 3, 2015 and entitled CONTROLLED ACTIVATION INGESTIBLE IDENTIFIER; U.S. Provisional Application 60/862,925 filed on Oct. 25, 2006 and entitled CONTROLLED ACTIVATION PHARMA-INFORMATICS SYSTEM; and PCT Patent Application Publication No. WO 2008/052136 and published on Oct. 23, 2008 and entitled CONTROLLED ACTIVATION INGESTIBLE IDENTIFIER.

FIELD OF INVENTION

The present invention relates to electronic devices and, more specifically, to electronic devices with a particle power source that are secured to a pharmaceutical product.

BACKGROUND

Capsules are made of a material that becomes gel-like once in contact with fluids. Such gel-like materials can interfere with the operation of an ingestible device, which is carried inside the capsule, with dissolvable components and electronic components. For example, gelatinous materials have low conductivity and, hence, if the device operates using conduction through fluids, then it will not operate properly. Thus, it is important to prevent the gel-like material of the capsule, as it is dissolving, from coming into contact with the device's components.

Additionally, capsules contain pharmaceutical materials that can interact with or damage the device during long term storage. For example, the product inside the capsule may be acidic and harmful to the electronic components. Alternatively, the content may be too basic, which can also harm the electronics. Furthermore, the material or product within the capsule will start to interact with the surrounding fluids, once the capsule is ingested and the capsule starts to disintegrate. The content of the capsule may include material, such as a drug or excipient or compound, that when dissolved at high concentrations, will interfere with the operation of the ingested device placed within the same capsule. As the material enters the solution at the site where the capsule is dissolving, there is a high concentration localized around the device. The stomach motion and diffusion disperses the capsule content throughout the stomach and reduces the concentration. During this time, the device will not operate properly if activated in the localized high concentration areas. Thus, the activation of the device needs to be delayed and the device should be protected from the capsule dissolving or disintegrating.

Thus, the devices need to be protected from the surrounding environment, including the content of the capsule as well as moisture. Furthermore, a manufacturing solution is needed to allow for manufacturing of these devices and placement of same within a capsule in such a manner that does not damage the device. Therefore, what is needed is suitable system and manufacturing process that protects the devices.

SUMMARY

The present disclosure includes a system and a manufacturing process that protects the device and allows for placement or combination of the device within a pharmaceutical product or capsule. The system includes circuitry and components that can be placed within certain environments. The device includes an assembly including an electronic unit, a flexible membrane secured to the unit, and a protective coating.

In one aspect of the present disclosure, a pharmaceutical product includes: (i) a capsule having an upper end and a lower end, wherein the upper and lower ends are brought together to form a housing that defines a cavity and wherein the cavity is filled with a drug, the capsule configured to disintegrate when in contact with a surrounding fluid, and (ii) an ingestible device associated with the capsule to encode information in a current signature, wherein the ingestible device is placed within the housing, wherein the ingestible device comprises electronic components that are surrounded by a protective layer, wherein the protective layer is configured to begin to disintegrate after the capsule has disintegrated and has exposed the content of the capsule to the surrounding fluids.

In another aspect of the present disclosure, a pharmaceutical product includes: (i) a housing that defines a cavity, wherein the cavity stores a pharmaceutical material, and wherein the housing comprises a material configured to dissolve based on contact with a fluid, (ii) an ingestible device to encode information in a current signature, wherein the ingestible device is positioned within the housing, and (iii) a protective material that encompasses the ingestible device.

In yet another aspect of the present disclosure, a pharmaceutical product includes: (i) a soluble structure comprising a pharmaceutical material, (ii) an electronic unit to encode information in a current signature, wherein the electronic unit is secured within the soluble structure, and (iii) a protective material that surrounds the electronic unit, wherein the protective material is configured to dissolve based on contact with a fluid.

Notwithstanding the claims, the present invention is also defined by the following clauses.

Clause 1: A process for creating a pharmaceutical product, the process comprising the steps of:

creating a device sheet including a plurality of devices;
securing an upper sheet to one side of the device sheet to produce a partially coated device sheet;
securing a lower sheet to another side of the partially coated device sheet, to produce a protected device sheet, wherein the upper sheet and the lower sheet form a protective layer;
separating a protected device from the protected device sheet; and
combining the protected device with a pharmaceutical agent to produce the pharmaceutical product.

Clause 2: The process of clause 1, wherein the device sheet defines a plurality of holes surrounding each device.

Clause 3: The process of clause 2, wherein the step of securing the lower sheet to another side of the partially coated device sheet includes the step of heating the lower sheet and the upper sheet such that the lower sheet comes into contact with the upper sheet through the holes, the lower sheet surrounding each device and the upper sheet and lower sheet secured to one another at the point of the contact.

Clause 4: The process of any of clauses 1-3, wherein the step of separating includes the steps of:
aligning the protected device sheet with an opening defined within a die such that the protected device is aligned with the opening of the die; and
punching the protected device using a punch through the opening and into a capsule placed within a capsule holder.

Clause 5: The process of any of preceding clauses, wherein the step of separating includes the steps of:
aligning the protected device sheet with an opening defined by a tray such that the protected device of the protected device sheet is aligned with the opening of the tray;
separating the protected device from the protected device sheet using a punch; and
placing the protected device into the opening of the tray.

Clause 6: The process of clause 5, further comprising the step of aligning the opening of the tray that comprises the protected device with a capsule holder that defines a plurality of cavities that hold a first end of a capsule, wherein the capsule includes the first end and a second end.

Clause 7: The process of clause 6, further comprising the step of pushing the protected device out of the opening of the tray and into the first end of the capsule placed within the cavity of the capsule holder.

Clause 8: The process of clause 7, wherein the step of combining includes the steps of:
filling the first end of the capsule that includes the protected device with a pharmaceutical product; and
securing the second end of the capsule to the first end of the capsule.

Clause 9: A device for placement within a capsule, the device comprising:
an assembly including:
a unit to encode information in a current signature, the unit comprising a partial power source; and
a flexible membrane secured to the unit, wherein the membrane engages the capsule's wall and holds the device in place within the capsule.

Clause 10: The device of clause 9, further comprising a protective coating surrounding the assembly.

Clause 11: The device of clause 9 or 10, further comprising a first protective sheet secured to an upper surface of the assembly and a second protective sheet secured to a lower surface of the assembly.

Clause 12: The device of clause 11, wherein the first protective sheet and the second protective sheet are secured to each other through a plurality of holes defined by the flexible membrane.

Clause 13: The device of clause 11 or 12, wherein the first protective sheet and the second protective sheet are secured to each other at the edge of the assembly and extend beyond the perimeter of the assembly such that the assembly is enclosed within the protective sheets.

Clause 14: The device of any of clauses 9-13, wherein the unit includes:
a first material secured to a support structure; and
a second material secured to the support structure and electrically isolated from the first material, such that the first material and second material represent a chemical voltage potential when in contact with a conducting fluid.

Clause 15: The device of clause 14, wherein the support structure comprises a control module electrically connected to the first material and the second material to control the conductance between the first material and the second material, wherein the control module encodes the information in the current signature by altering the conductance.

Clause 16: The device of any of clauses 9-15, wherein the flexible membrane includes a plurality of legs that engage the capsule's wall when the assembly is pressed into the capsule.

Clause 17: The device of any of clauses 9-16, wherein the flexible membrane includes a plurality of extensions shaped to fit within the capsule and hold the assembly in place.

Clause 18: A pharmaceutical product comprising:
a capsule having an upper end and a lower end, wherein the upper and lower ends are brought together to form a housing that defines a cavity and wherein the cavity is filled with a drug, the capsule configured to disintegrate when in contact with a surrounding fluid; and
an ingestible device associated with the capsule, preferably a device according to any of the clauses 9-17, to encode information in a current signature, wherein the ingestible device is placed within the housing, wherein the ingestible device includes electronic components that are surrounded by a protective layer, wherein the protective layer is configured to begin to disintegrate after the capsule has disintegrated and has exposed the content of the capsule to the surrounding fluids.

Clause 19: The product of clause 18, further comprising a flexible membrane that is secured to the ingestible device to produce an assembly wherein the flexible membrane positions the assembly within the capsule.

Clause 20: The product of clause 19, further comprising a first protective sheet secured to an upper surface of the assembly and a second protective sheet secured to a lower surface of the assembly, wherein the first protective sheet and the second protective sheet are secured to each other and surround the assembly.

DESCRIPTION OF THE DRAWINGS

FIG. 1 shows a capsule with a laminated device inside the capsule.

FIG. 2A shows a capsule with a table inside the capsule and the tablet includes a covered device.

FIG. 2B shows a capsule with a table inside the capsule and the tablet includes a device.

FIG. 3 shows a capsule with a covered device inside one portion of the capsule.

FIG. 4A shows an example of a device that can be used in the capsule of FIG. 3.

FIG. 4B shows another example of a device that can be used in a capsule end for FIG. 3 with a specific designed capsule end to mechanically hold the device in place.

DETAILED DESCRIPTION

Figure 5:
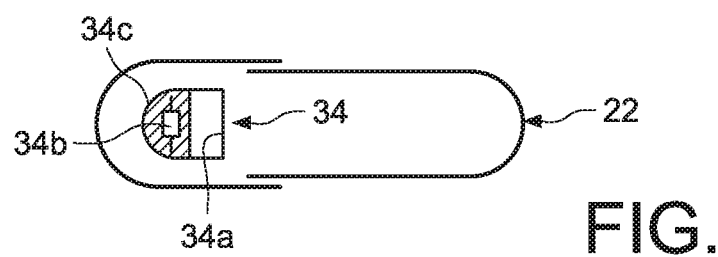
FIG. 5 shows a device with a cover secured onto a tablet and the tablet placed inside a capsule.

The present invention discloses multiple approaches to protecting a device from the harmful effects of a capsule and the content of the capsule when the device is placed within the capsule. The present invention also discloses multiple approaches to securing the device within the capsule that contains the product. The scope of the present invention is not limited by the type of product within the capsule. For example, the product can be a capsule, a time-release oral dosage, a powder, a gel, a sub-lingual tablet or any oral dosage product. In accordance with one aspect of the present invention, the capsule has the device positioned inside or secured to the interior. In an alternative arrangement, the device is secured to the exterior of the capsule or as part of the capsule wall.

In accordance with the teachings of the present, in some embodiments, the device is placed within the capsule. In accordance with other aspects of the present invention, the device is secured with the capsule. Various methods of securing the device to the capsule are disclosed. For example, the device may be secured to the capsule using ingestible glues, pressure sensitive adhesives, thermal adhesives, mechanically attached, secured to a band that is later placed around the product.

In addition to the methods used to secure the device to the product, there are various methods of coating or laminating the device, surrounding the device, or separating and isolating the device from the drug or product within the capsule to prevent a reaction between the device and the drug or product. For example, certain products contain acids that can damage the device, such as tartaric acid. Additionally, there are times when the device, upon activation may interact with the product or drug when the device is activated too quickly. Thus, as discussed in detail below, there are various lamination and packaging options that may be used in association with the device to prevent such problems.

Referring now to FIG. 1, an ingestible device 20 is shown with a layer 20a surrounding electronics 20b. The layer 20a is soluble and a disintegrating layer of material around the electronics 20b. The layer 20a delays the exposure of the electronics 20b to surrounding fluids. The device 20 is placed inside the capsule 22, which also contains a pharmaceutical product or drug. The capsule 22 has a bottom end 22a and a top end 22b. The capsule 22 is made of a dissolvable material, such as gelatin. Upon ingestion, the capsule 22 walls turn into a gel-like material, due to contact with fluids. The layer 20a prevents contact between the gel-like material of the capsule 22 and the electronics 20b until the gel-like material has dissolved and no longer interferes with the operation of the device 20. During the time the capsule 22 is dissolving, the layer 20a is also slowly disintegrating away to allow the electronics 20b to come into contact with the fluids and become activated. One example of the type of electronic components that are part of the device 20 is disclosed in U.S. patent application Ser. No. 12/564,017 filed on Sep. 21, 2009, which issued on Jul. 12, 2011 as U.S. Pat. No. 7,978,064 and is titled COMMUNICATION SYSTEM WITH PARTIAL POWER SOURCE, the entire disclosure of which is incorporated herein by reference. The capsule 22, in all instances described herein is intended to carry a drug and includes a drug product in addition to the device.

Referring now to FIGS. 2A and 2B, in accordance with another aspect of the present invention, the capsule 22 is shown with a device 24 inside the capsule. The device 24 includes a disintegrating film or material 24a and components and electronics 24b. In accordance with one embodiment, the device 24 has a laminated coating as shown in FIG. 2A. In accordance with another embodiment, the device 24 has is surrounded by the material 24a as shown in FIG. 2B. As the capsule 22 is ingested, the capsule ends 22a and 22b disintegrate or dissolve. The content of the capsule 22 comes into contact with the surrounding fluids. The material 24a reacts with the fluids to prevent the gel-like material of the capsule 22 from coming into contact with the electronics 24b as discussed with respect to FIG. 2.

Referring now to FIG. 3, the capsule 22 is shown with a device 26 positioned within the capsule end 22b in accordance with another aspect of the present invention. The device 26 is held in position inside the capsule end 22b using friction or by a mechanical means as will be discussed with respect to FIGS. 4A and 4B, respectively. In accordance with various aspects of the present invention, the device 26 may be covered in a manner similar to the device 20 or the device 24 of FIG. 1 and FIGS. 2A and 2B, respectively. For example, the device 26 may include a layer or lamination material or the device 26 may include a disintegration material. As noted, the device 26 is held in position using friction or mechanical attachment.

Referring now to FIG. 4A, in accordance with one aspect of the present invention, the device 26 includes tabs or legs 28 and electronics 26b. The legs 28 are flexible and as the device 26 is pushed into the capsule end 22b, the friction between the legs 28 and the wall of the capsule end 22b hold the device 26 in place. As the capsule 22 dissolves, the walls of the capsule end 22b change shape or collapse causing the friction between the legs 28 and walls of the capsule end 22b to reduce and thereby allow the device 26 to be released from the capsule end 22b.

Referring now to FIG. 4B, in accordance with another aspect of the present invention, the device 26a includes tabs or legs 30 and electronics 26b. The legs 30 are used to secure the device 26a into a capsule end 22c. The capsule end 22b of FIG. 3 is replaced with the capsule end 22c. The capsule end 22c includes a matching number of slots or indentations 32 to the legs 30 of the device 26a. In an alternative aspect of the present invention, the number of legs 30 may differ from the number of slots 32. As the device 26a is pressed inside the capsule end 22c, the tabs 30 engage the slots 32 and lock the device 26a into place mechanically. As the capsule end 22c dissolves, the walls of the capsule end 22c change shape or collapse causing the device 26a to be released from the capsule end 22c.

Referring now to FIG. 5, the capsule 22 is shown with device 34 in accordance with another aspect of the present invention. The device 34 includes a material 34a to which is secured electronics 34b, similar to the electronics 24b, and a layer or covering 34c.

Figure 6:
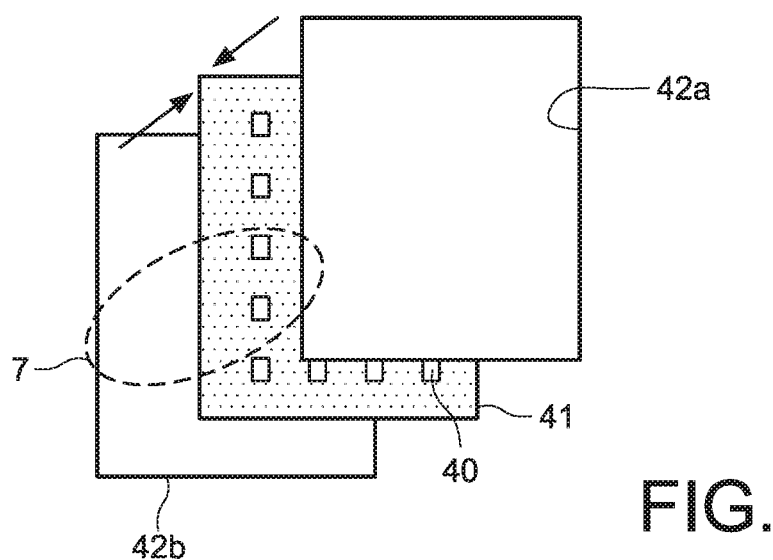
FIG. 6 shows the process of laminating or covering the device.
Figure 7:
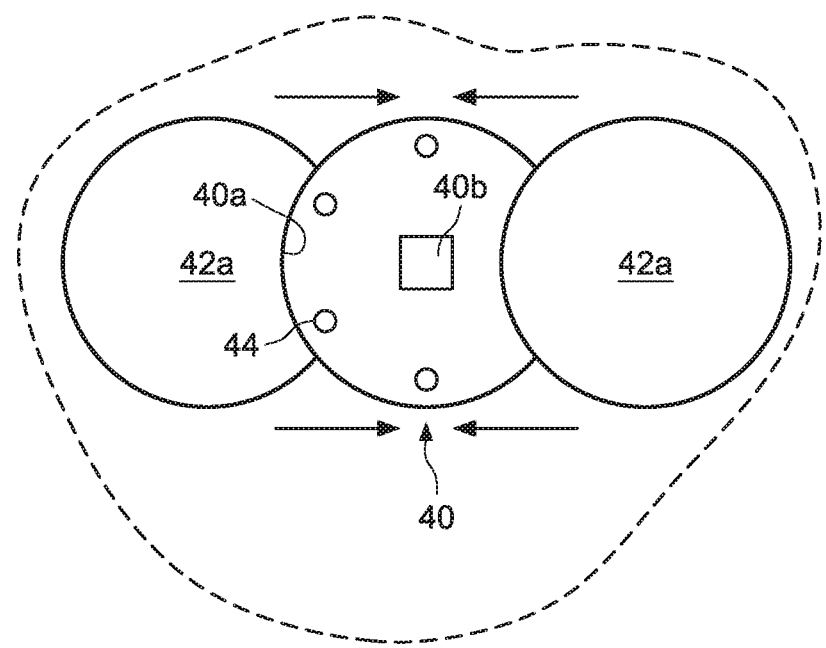
FIG. 7 shows a closer view of the assembly pieces of FIG. 6.

Referring now to FIG. 6 and FIG. 7, a process for creating a device with a covering or lamination is shown in accordance with one aspect of the present invention. Devices 40 are shown on a sheet 41 that is placed between a top lamination sheet 42a and a bottom lamination sheet 42b. The sheets 42a and 42b may be made of a variety of materials or films, such as polymer films that include polyethylene oxide, hydroxypropyl cellulose, and triethyl citrate. Other films that can be used include any solulable polymer, plasticizer. The film provides a moisture barrier and dissolves under the proper conditions to delay activation of the device. The film layer is designed to provide sufficient delay in exposure of the device to the surrounding fluids relative to the disintegration and dispersion of the capsule material and the content of the capsule. The film layer may includes the soluble materials, barrier materials (such as lipids, polyvinyl alcohol), processing aids (such as plasticizers, adhesion promoters), and stabilizers. Furthermore, the film layer may be manufactured via lamination, application of a coating solution or slurry followed by a cure. In accordance with other aspects of the present invention, the film or layer may be similar to FIG. 2 and formed using dry compression, such as a tablet press.

There are a variety of active agents or pharmaceutical products that can be placed inside of a capsule. For example, there are FDA approved drugs, drugs that are disclosed chemically in a patent application or in an issued patent, there are drugs are disclosed in the Orange Book as part of the approved drug products, and generics. In accordance with the teachings of the present inventions, any one or combination of such drugs may be placed within the capsule along with the device. Each of those drugs will have a specific and unique impact on the operation of the device as well as the disintegration of the film used because of the unique chemical composition. As such, the type of material uses as the film layer will vary to be compatible to the chemical composition of the products used. Thus, the scope of the present invention is not limited by the type of content of the capsule and the film or coating layer around the electronic components of the device.

In accordance with another aspect and benefit of the present invention, the film or coating will also prevent the interaction components of the device with the drug inside the capsule and as such the device will not alter or impact the effectiveness of the drug.

As shown in FIG. 7, one example of the device 40 includes a skirt 40a with a plurality of holes 44 and electronics 40b. As the sheets 42a and 42b are subject to heating or pressure, then the sheets 42a and 42b are secured to each other through the holes 44 and the device 40 is securely held between the sheets 42a and 42b. As shown in FIG. 7, the device 40 is laminated between the sheets 42a and 42b. In accordance with another aspect of the present invention, the sheets 42a and 42b may have the portions for each device 40 punched, cut-out, or removed first and then positioned above and below the device 40. The portions are cut to be oversized. Thus, as the portions of the sheets 42a and 42b are exposed to heat or pressure, then the oversized portions at the edges are secured to each other forming a pocket that surrounds the device 40 as well as secured to in place through the holes 44 as noted above. In accordance with another aspect of the present invention, the holes 44 may be eliminated when the device is placed between the oversized portions and secured within a pocket that surrounds the device 40.

Figure 8:
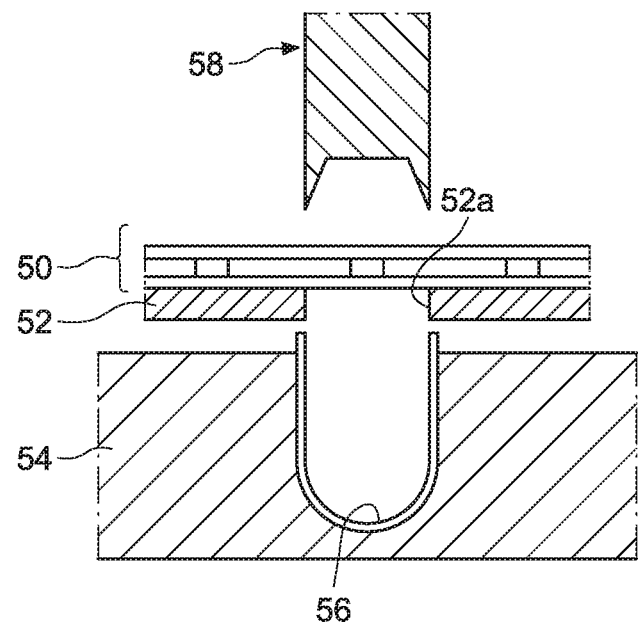
FIG. 8 shows a process of inserting a device within a capsule end in accordance with one aspect of the present invention.
Figure 9:
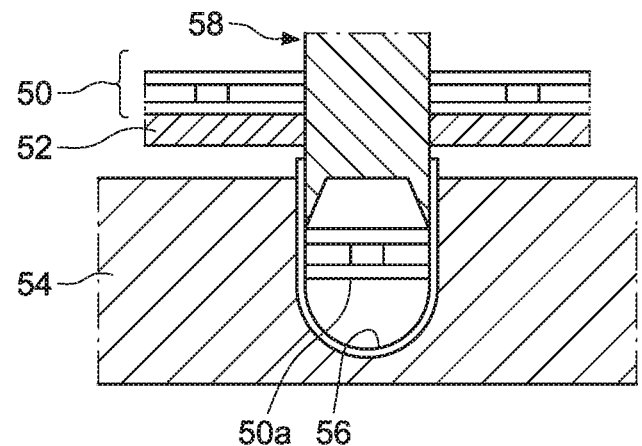
FIG. 9 shows an advanced stage of the process of FIG. 8.

Referring now to FIG. 8 and FIG. 9, in accordance with one aspect of the present invention, a laminated device sheet 50 is positioned above a die 52 with a hole 52a in the die 52. Even though only one hole 52a is shown, it will be understood by those skilled in art that the die may include multiple holes and the example discussed with respect one, may be repeated for many. The hole 52a of the die 52 is positioned above a capsule holder 54 that contains a capsule end 56. As the sheet 50 is positioned above the hole 52a, a punch 58 is used to cut the device 50a out of the sheet 50 and insert the device 50a into the capsule end 56. As noted above in accordance with various aspects of the present invention, the device 50a can have a variety of shapes and those shapes can be created by the punch 58.

Figure 10:
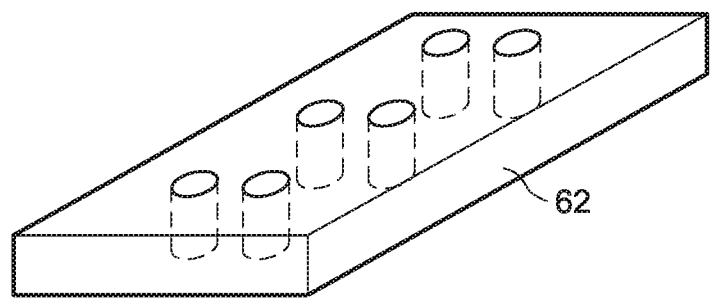
FIG. 10 shows a perspective view of a transfer tray.
Figure 11:
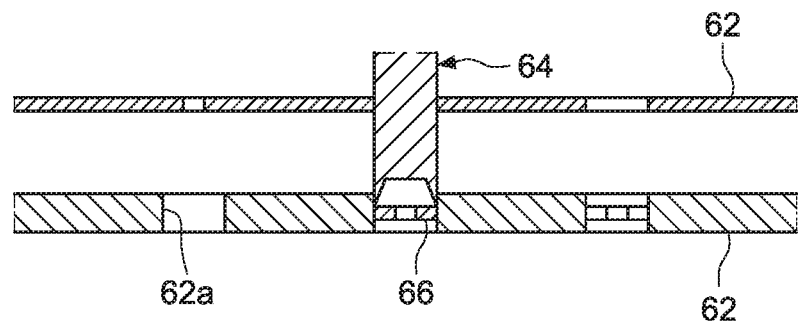
FIG. 11 shows an initial stage of the process of inserting a device within a capsule end in accordance with one aspect of the present invention.
Figure 12:
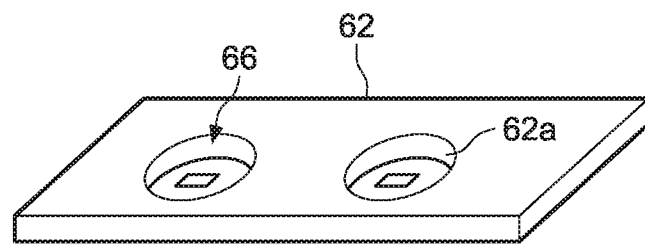
FIG. 12 shows the device of FIG. 11 within the transfer tray of FIG. 10.
Figure 13:
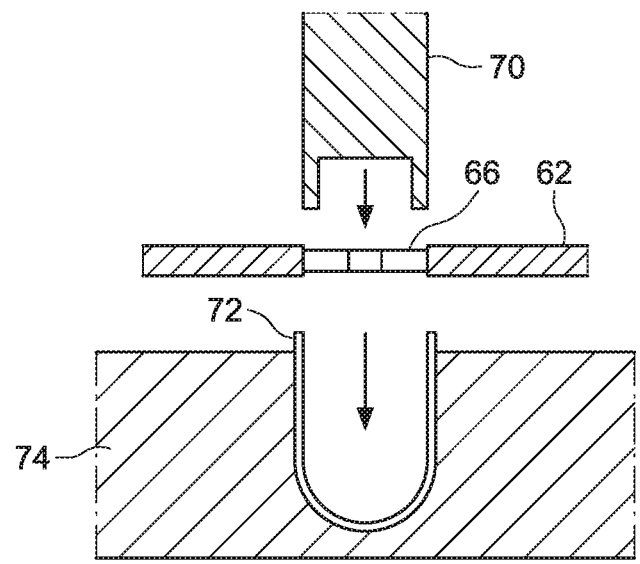
FIG. 13 shows an advanced stage of the process of FIG. 11 in accordance with one aspect of the present invention.
Figure 14:
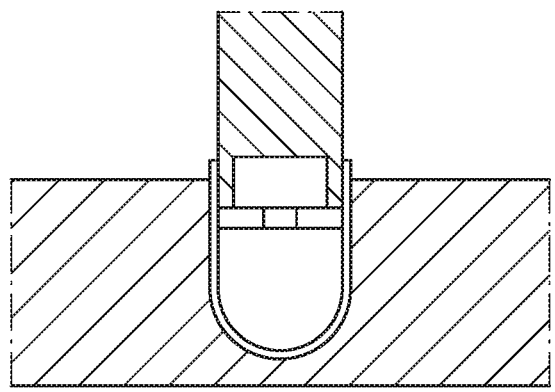
FIG. 14 shows an advanced stage of the process of FIG. 13 in accordance with one aspect of the present invention.

Referring now to FIGS. 10-14, in accordance with one aspect of the present invention, the device 40 of FIG. 6 may be punched out and placed inside a hole 62a of a transfer tray 62. The tray 62 is shown in FIG. 10 with a plurality of holes. As shown in FIG. 11, the tray 62 is positioned below a sheet of devices, such as the sheet 50 of FIG. 8. A punch blade 64 cuts a device 66 from the sheet of devices and inserts the device 66 into the hole 62a. The device 66 is held in place in the hole 62 with friction as shown in FIG. 12. The tray 62 is then advanced to the next step of the process and a punch press 70 pushes the device 66 into a capsule end 72 held within a capsule holder 74 as shown in FIGS. 13 and 14.

As noted above various disintegration materials may be used to surround the electronic components. For example, a disintegrant may be sodium starch glycolate or a water soluble excipient such as hydroxypropyl cellulose. It will also be apparent that the various layers disclosed can be eliminated or combined depending on the material employed and the properties thereof.

As described herein, a system of the present invention is used with a conducting fluid to indicate the event marked by contact between the conducting fluid and the system. For example, the system of the present disclosure may be used with a pharmaceutical product and the event that is indicated is when the product is taken or ingested. The term "ingested" or "ingest" or "ingesting" is understood to mean any introduction of the system internal to the in-vivo. For example, ingesting includes simply placing the system in the mouth all the way to the descending colon. Thus, the term ingesting refers to any instant in time when the system is introduced to an environment that contains a conducting fluid. Another example would be a situation when a non-conducting fluid is mixed with a conducting fluid. In such a situation the system would be present in the non-conduction fluid and when the two fluids are mixed, the system comes into contact with the conducting fluid and the system is activated. Yet another example would be the situation when the presence of certain conducting fluids needed to be detected. In such instances, the presence of the system, which would be activated, within the conducting fluid could be detected and, hence, the presence of the respective fluid would be detected.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A pharmaceutical product, comprising:
    a capsule having an upper end and a lower end, wherein the upper and lower ends are brought together to form a housing that defines a cavity and wherein the cavity is filled with a drug, the capsule configured to disintegrate when in contact with a surrounding fluid; and
    an ingestible device associated with the capsule to encode information in a current signature, wherein the ingestible device is placed within the housing, wherein the ingestible device comprises electronic components that are surrounded by a protective layer, the protective layer comprising a plurality of legs protruding outwardly from the electronic components, and wherein the protective layer is configured to begin to disintegrate after the capsule has disintegrated and has exposed the content of the capsule to the surrounding fluids.

2. The product of claim 1, wherein the plurality of legs are configured to hold the ingestible device in place within the housing by applying friction to one or more inner walls of the housing.

3. The product of claim 2, wherein either the upper end or the low end of the capsule comprises material within the cavity to define a plurality of slots that are configured to engage the plurality of legs of the ingestible device to lock the ingestible device into place mechanically.

4. The product of claim 3, wherein the number of legs in the plurality of legs differs from the number of slots in the plurality of slots.

5. The product of claim 1, wherein the protective layer is configured to prevent at least one of the capsule or the drug from interacting with the electronic components of the ingestible device.

6. The product of claim 1, further comprising:
    a flexible membrane that is secured to the ingestible device to produce an assembly wherein the flexible membrane positions the assembly within the capsule;
    a first protective sheet secured to an upper surface of the assembly; and
    a second protective sheet secured to a lower surface of the assembly, wherein the first protective sheet and the second protective sheet are secured to each other and surround the assembly.

7. The product of claim 6, wherein the delayed exposure delays activation of the ingestible device.

8. A pharmaceutical product, comprising:
    a housing that defines a cavity, wherein the cavity stores a pharmaceutical material, and wherein the housing comprises a material configured to dissolve based on contact with a fluid;
    an ingestible device to encode information in a current signature, wherein the ingestible device is positioned within the housing; and
    a protective material that encompasses the ingestible device, the protective layer comprising a plurality of legs protruding outwardly that are configured to hold the ingestible device in place within the housing by applying friction to one or more inner walls of the housing.

9. The product of claim 8, wherein the ingestible device further comprises at least one of electronic components or dissolvable components protected by the protective material.

10. The product of claim 8, wherein the ingestible device is attached to a flexible component, and wherein the flexible component is configured to releasably secure the ingestible device within the housing.

11. The product of claim 8, wherein the pharmaceutical material comprises at least one of a drug, an excipient, or a compound.

12. The product of claim 8, wherein the protective material encompasses the ingestible device by laminating or encasing the ingestible device, and wherein the protective material is configured to dissolve based on contact with the fluid.

13. The product of claim 12, wherein the protective material is configured to dissolve relative to the material of the housing to delay exposure of the ingestible device to the fluid.

14. The product of claim 8, wherein the protective material comprises two different materials.

15. A pharmaceutical product, comprising:
    a soluble structure comprising a pharmaceutical material;
    an electronic unit to encode information in a current signature, wherein the electronic unit is secured within the soluble structure; and
    a protective material that surrounds the electronic unit, the protective layer comprising a plurality of legs protruding outwardly from the electronic unit that are configured to hold the electronic unit in place within the soluble structure by applying friction to one or more inner walls of the soluble structure, wherein the protective material is configured to dissolve based on contact with a fluid.

16. The product of claim 15, wherein the soluble structure defines a cavity in which the electronic unit is secured in, and the soluble structure further comprises material within the cavity to define a plurality of slots that are configured to engage the plurality of legs of the protective material to lock the electronic unit into place mechanically.

17. The product of claim 15, wherein the protective material is configured to dissolve relative to the soluble structure to delay exposure of the electronic unit to the fluid.

18. The product of claim 15, wherein the protective material is configured to prevent the pharmaceutical material from interacting with a component of the electronic unit.

19. The product of claim 15, wherein the protective material comprises a first sheet and a second sheet, and wherein the first sheet is secured to the second sheet to form a pocket that surrounds the electronic unit.

20. The product of claim 19, wherein the electronic unit is attached to a flexible skirt comprising a plurality of holes, and wherein the first sheet is further secured to the second sheet through the plurality of holes to secure the electronic unit within the pocket.

* * * * *